US011077296B2

(12) United States Patent
McCabe et al.

(10) Patent No.: US 11,077,296 B2
(45) Date of Patent: Aug. 3, 2021

(54) IMPLANT CONDUCTOR ASSEMBLY WITH IMPROVED RADIO FREQUENCY PROPERTIES

(71) Applicant: WAIKATOLINK LIMITED, Hamilton (NZ)

(72) Inventors: Steven Owen McCabe, Porirua (NZ); Jonathan Brereton Scott, Hamilton (NZ)

(73) Assignee: WAIKATOLINK LIMITED, Hamilton (NZ)

(*) Notice: Subject to any disclaimer, the term of this patent is extended or adjusted under 35 U.S.C. 154(b) by 111 days.

(21) Appl. No.: 15/775,243

(22) PCT Filed: Nov. 16, 2016

(86) PCT No.: PCT/NZ2016/050182
§ 371 (c)(1),
(2) Date: May 10, 2018

(87) PCT Pub. No.: WO2017/086805
PCT Pub. Date: May 26, 2017

(65) Prior Publication Data
US 2018/0326202 A1    Nov. 15, 2018

(30) Foreign Application Priority Data
Nov. 16, 2015  (NZ) .................................. 714212

(51) Int. Cl.
*A61N 1/05*  (2006.01)
*A61N 1/08*  (2006.01)
(Continued)

(52) U.S. Cl.
CPC .............. *A61N 1/05* (2013.01); *A61N 1/06* (2013.01); *A61N 1/086* (2017.08); *A61N 1/3605* (2013.01)

(58) Field of Classification Search
USPC ........................................................ 607/116
See application file for complete search history.

(56) References Cited

U.S. PATENT DOCUMENTS

| 8,825,179 B2 | 9/2014 | Walker et al. |
| 2006/0089697 A1* | 4/2006 | Cross, Jr. ............... A61N 1/056 607/122 |

(Continued)

FOREIGN PATENT DOCUMENTS

| EP | 1161276 A1 | 12/2001 |
| WO | 00/54833 A1 | 9/2000 |

OTHER PUBLICATIONS

Extended European Search Report dated Jul. 2, 2019, EP Application No. 16866727.7, pp. 1-6.
(Continued)

*Primary Examiner* — Nicole F Lavert
(74) *Attorney, Agent, or Firm* — MH2 Technology Law Group LLP (57) ABSTRACT

In one aspect the invention provides an implant conductor lead assembly which includes an electrode lead, and at least one field target conductor. The field target conductor(s) is located adjacent to the electrode lead to mutually couple the field target conductor to the electrode lead. The electrode lead acts to concentrate electromagnetic fields in the vicinity of the implant conductor assembly towards the field target conductor or conductors.

21 Claims, 9 Drawing Sheets

(51) Int. Cl.
 *A61N 1/06* (2006.01)
 *A61N 1/36* (2006.01)

(56) References Cited

U.S. PATENT DOCUMENTS

| | | |
|---|---|---|
| 2008/0243218 A1 | 10/2008 | Bottomley et al. |
| 2010/0228331 A1* | 9/2010 | Conger .................. A61N 1/05 607/122 |
| 2011/0230943 A1* | 9/2011 | Johnson .................. A61N 1/05 607/116 |
| 2012/0109270 A1 | 5/2012 | Foster |
| 2013/0204337 A1* | 8/2013 | Wahlstrand .......... A61N 1/0534 607/117 |
| 2015/0057730 A1 | 2/2015 | Wahlstrand et al. |

OTHER PUBLICATIONS

McCabe et al., "Cause and Amelioration of MRI-Induced Heating Through Medical Implant Lead Wires", In 21st Electronics New Zealand Conference (ENZCon), 2014, 7 pages.

McCabe et al., "A Novel Implant Electrode Design Safe in the RF Field of MRI Scanners", IEEE Transactions on Microwave Theory and Techniques, 2017, 7 pages.

Kiran Karve (Authorized Officer), International Search Report dated Apr. 28, 2017, International Application No. PCT/NZ2016/050182, filed Nov. 16, 2016, 16 pages.

\* cited by examiner

IMPLANT CONDUCTOR ASSEMBLY WITH IMPROVED RADIO FREQUENCY PROPERTIES

CROSS REFERENCE TO RELATED APPLICATIONS

This application is a U.S. National Stage entry of PCT/NZ2016/050182, Nov. 16, 2016, which claims priority to NZ Application No. 714212, filed Nov. 16, 2015, the contents of all of which are hereby incorporated by reference in their entirety.

FIELD OF THE INVENTION

This invention relates to an implant conductor assembly with improved radio frequency properties. Preferably the invention may be used to minimise the induction of radio frequency currents within an electrode lead of an implant conductor assembly.

BACKGROUND OF THE INVENTION

A variety of therapeutic devices have been developed to deliver bioelectrical stimulation therapies. These devices are surgically implanted into the body of a patient and normally incorporate control electronics connected to a power supply system such as a battery pack. As these components can be relatively large they may be sited within a user's body some distance from an organ, muscle or structure requiring bioelectrical stimulation. An implant electrode lead commonly needs to be run through the body from the power and control electronics to the region requiring bioelectrical stimulation.

Surgical implant manufacturers select implant conductors which exhibit low electrical resistance to direct currents. This selection minimises the voltage required to generate therapeutic currents while also maximising implant battery lifespans.

However, the presence of surgical implants creates a patient safety issue with the use of Magnetic Resonance Imaging (MRI) machines. The operation of MRI scanning machines involves:
  A large magnetic field,
  A varying magnetic field in the kilohertz range which induces eddy currents,
  An RF field operating at the 50-250 megahertz range.

MRI machines are carefully designed and used under strict operational protocols to avoid inadvertent heating of patient body tissues. The high frequency RF field can produce longitudinal electrode lead currents at RF frequencies which result in heating effects in the lead conductors and the electrodes.

Surgically implanted conductors act as antennas within the body and concentrate the strong radio frequency fields generated by an MRI machine. This can result in high temperatures at the electrode end of the implant as its lead is exposed to the MRI field. This is a significant patient safety problem when the length of the implant conductor is approximately equal to an odd integer multiple of the half wavelength at the electric field frequency—for example—$\lambda/2$, $3\lambda/2$, $5\lambda/2$ etc.

One attempt to address these problems with implant leads and MRI machines is disclosed in U.S. Pat. No. 8,364,286. This document describes an implant lead assembly which employs a Faraday shield to surround and encapsulate an implant electrode lead. This technology aims to shield the electrode lead from local electromagnetic fields and thereby decrease the heating effects experienced by the lead.

However, the size and dimensions of implant conductor assemblies cause manufacturing complications for the technology described above. In particular, these forms of electrode lead shields must be formed on the same small scale as the electrode leads used and must fully enclose and wrap closely around the electrode lead to function effectively. These requirements therefore make the resulting implant conductor assembly difficult and expensive to manufacture.

It would therefore be of advantage to have available an improved implant conductor technology which addressed or mitigated the above problems, or at the very least provided an alternative choice over the current prior art. It would be of particular advantage to have an inexpensive implant conductor assembly with improved radio frequency properties targeted at minimising the induction of radio frequency currents within an implant conductor electrode lead.

DISCLOSURE OF THE INVENTION

According to one aspect of the present invention there is provided an implant conductor assembly which includes an electrode lead, and at least one field target conductor located adjacent to the electrode lead to mutually couple the field target conductor to the electrode lead, wherein the electrode lead acts to concentrate electromagnetic fields in the vicinity of the implant conductor assembly towards said at least one field target conductor.

According to a further aspect of the present invention there is provided an implant conductor assembly substantially as described above wherein said at least one field target conductor is positioned with its longitudinal axis parallel to the longitudinal axis of the electrode lead, the longitudinal axis of said at least one field target conductor and the electrode lead being offset from each other.

The present invention is arranged to provide an implant conductor assembly for use in combination with surgical implant technology, and will be referred to in various embodiments to as providing part of a surgical implant. Reference in general will also be made throughout this specification to this implant conductor assembly being used with a bioelectrical stimulation implant. In these applications an implant conductor assembly can include an electrode lead formed from a length of conductive material which has one end defining an electrode and an opposite end defining a supply terminal.

Those skilled in the art will however appreciate that the implant conductor assembly provided by the invention may be used in other applications if required. In particular the invention may be used with implants which need not necessarily provide a bioelectrical stimulation effect nor provide an implant conductor with one end forming an electrode or alternatively a supply terminal.

Furthermore the invention may potentially be used in combination with surgical implants installed in both humans and/or in animals. Those skilled in the art will appreciate that references made to implant technology does not restrict the use of the present invention to human recipients only.

Reference throughout this specification will also be made to an electrode lead provided with the invention being formed from an existing or prior art electrode lead. For example, in some embodiments an electrode lead may be formed from a structure which integrates a plurality of electrode conductors each being capable of performing as an electrode. In yet another embodiment an electrode lead may simply incorporate one such electrode conductor. The implant conductor assemblies provided by the invention incorporate one or more field target conductors to minimise or attenuate the induction of radio frequency electrical currents in such prior art electrode leads.

A field target conductor employed with the invention is located adjacent to the electrode lead at a position which promotes mutual coupling of the electrode lead to the field target conductor. The adjacent positioning of the field target conductor offsets the longitudinal axis of the electrode lead from the longitudinal axis of the field target conductor.

This may be contrasted with prior art implant conductor assemblies which employ a shield material wrapped around and enclosing an electrode conductor. With such prior art arrangements the longitudinal axis of the shield material is aligned with and therefore not offset from the longitudinal axis of the electrode lead. Conversely, with the present invention a field target conductor is positioned with its longitudinal axis parallel to the longitudinal axis of the electrode lead, each longitudinal axis being offset from the other.

The adjacent positioning of the field target conductor to the electrode lead and the mutual coupling of these elements results in the electrode lead concentrating electromagnetic fields in the vicinity of the assembly towards the field target conductor. The electrode lead—which normally experiences detrimental induced radio frequency currents—operates in the invention to direct and reflect electromagnetic fields so that field intensity is experienced by the field target conductor at the expense of the electrode lead. This effect is achieved by tailoring the size, length or dimensions of any field target conductor relative to the form of the electrode lead provided by the invention. In practice the assembly provided by the invention may be described in terms of electromagnetic field antenna terminology, where the electrode lead acts as a mutually-coupled element with the field shaped towards the field target conductor after the fashion of 'reflector' and 'director' elements acting in a multi-element antenna.

In a preferred embodiment the length of a field target conductor may be less than the length of the electrode lead.

In some embodiments this length differential may be as small as half the wavelength of the expected electromagnetic field to which the assembly is to be exposed.

In various embodiments a range of field conductor lengths may be used. For example, in some embodiments a field target conductor can have a length in the range of 40% to 90% of the length of the electrode lead. In further embodiments a field target conductor may have a length in the range of 50% to 70% of the length of the electrode lead, while yet in other preferred embodiments a field target conductor can have a length approximately equal to 60% of the length of the electrode lead. Those skilled in the art will appreciate that the length of the field target conductor used can vary to suit the required performance of the invention, the type or types of MRI scanner machines the assembly is to be exposed to and potentially the materials used to construct the conductor.

Those skilled in the art will also appreciate that an implant conductor assembly provided by the invention may include only one field target conductor in some instances, while in other embodiments two or potentially more field target conductors may be provided adjacent to an electrode lead.

For example, in one embodiment a single field target conductor may be located adjacent to one side of an electrode lead, and may preferably extend approximately 60% of the length of the electrode lead.

In another embodiment a pair of field target conductors may be provided in conjunction with implant conductor lead assembly. In preferred embodiments of this form these two field target conductors can be located on opposite sides of the same electrode lead.

In such embodiments the pair of conductors can exhibit a range of lengths, and need not necessarily be of the same length. For example, in some instances these field target conductors may extend at least 40% of the length of the electrode lead, while in other embodiments they may exhibit lengths extending at least 60% of the length of the electrode lead. In yet other implementations one or both of this pair of field target conductors may extend approximately 90% of the length of the electrode lead.

Again those skilled in the art will appreciate that the length of the field target conductors used can vary to suit the required performance of the invention, the type or types of MRI scanner machines the assembly is to be exposed to and potentially the materials used to construct the conductor.

In yet other embodiments discrete linear arrays of relatively short field target conductors may be located adjacent to one side of an electrode lead, with multiple short conductors running the same length as an equivalent single long conductor. In further alternative embodiments multiple linear arrays of short field target conductors can be located on opposite sides of an electrode lead, with again the multiple short conductors running the same length as an equivalent single long conductor.

Furthermore, in additional embodiments a field target conductor may be optimised to perform effectively when exposed to the emissions of one specific type of MRI scanning machine, or a set of two or more types of MRI machines operating at different frequencies. For example, in some embodiments an implant conductor assembly may include a set of one or more field target conductors optimised to mitigate heating effects when exposed to the field of a 1.5 T/64 MHz MRI scanner, and can also include a second set of one or more field target conductors optimised to mitigate heating effects when exposed to the field of a 3 T/128 MHz MRI scanner. In yet other embodiments an implant conductor assembly may be provided with one or more field target conductors optimised to mitigate heating effects when exposed to the fields of both 1.5 T/64 MHz and 3 T/128 MHz MRI scanners.

A field target conductor may be formed from materials currently employed as existing prior art implant conductors. In various embodiments the conductive material selected may exhibit desirable electrical characteristics while minimising patient tissue rejection or irritation effects.

In preferred embodiments a field target conductor may be formed from a length of conductive material. This conductor will therefore have a longitudinal length dimension which is substantially greater than its cross-section width. The field target conductor will define an exterior surface which extends between each end of the length of conductive material.

Those skilled in the art will appreciate that various arrangements of conductive materials may be used to form lengths of field target conductor. In a range of embodiments a field target conductor may be formed by any arrangement of conductive components, such as a solid length of conductor, multi-stranded wire or alternatively woven conductive filaments or fibres. In various embodiments these filaments may have either a substantially solid or hollow cross section profile.

In a preferred embodiment a field target conductor may exhibit a substantially uniform transverse cross-section profile along its entire length. Reference throughout this specification will also be made to the field target conductor being provided with this uniform character, although those skilled in the art will appreciate that other arrangements and physical dimensions are also within the scope of the invention.

In a preferred embodiment at least a portion of the exterior surface of a field target conductor may be exposed to the body tissue of the recipient of the assembly.

For example, in one embodiment at least the mid-point or middle section of the length of the conductor is exposed to the body tissue of the implant recipient. Alternatively, in other embodiments substantially all of the exterior surface of the field target conductor may be exposed to the tissue of an implant recipient. However in yet other embodiments the ends of a field target conductor may be sealed inside an electrically insulating material.

In various embodiments the physical characteristics of the material used to provide a field target conductor may be optimised for its role as part of the surgical implant. In a preferred embodiment a field target conductor may be provided with an electrical resistance ranging from 10-100000 Ohms/meter.

In a preferred embodiment at least one field target conductor is formed of a material having increased electrical resistance such that the energy of an MRI field is dissipated substantially evenly throughout the at least one field target conductor.

For example, in various embodiments the material used to form such a conductor may be selected for relatively high electrical resistance—such as that provided by low conductivity metals or various composite materials—which are still able to perform effectively as field target conductors. An increased electrical resistance allows the energy of an MRI field directed into a target field conductor to be dissipated evenly throughout its length as heat at temperatures which are unlikely to damage body tissues. A range of materials may be used in various embodiments to provide such electrical resistance improvements, including—but not limited to—gold, platinum, iridium, rhodium and their alloys, as well as silver cored wires, titanium, tungsten and/or stainless steel.

In yet other embodiments the physical structure and/or electrical connections made by a field target conductor may be optimised to maximise the effective surface area of the conductor. In such embodiments it is preferable to maximise the exposure of the surface of a field target conductor to the tissue of an implant patient. Surface area increases improve the electrical coupling experienced between the field target conductor and these tissues, allowing energy absorbed by the target conductor to be dissipated into the surrounding patient tissues. Surface area increases may be produced by selecting a broad diameter target field conductor, roughening the surface of such a conductor, or potentially in some instances by connecting the end of the conductor furthest from the electrode of the implant to other internal implant components, such as an impulse generator housing.

The present invention may therefore provide potential advantages over the prior art or at least provide an alternative choice to the existing prior art.

The invention adds at least one field target conductor to various forms of prior art implant electrode leads. The addition of a field target conductor therefore improves the resulting implant assembly without requiring any significant modifications to these prior art implant electrode leads.

The invention can be used to mitigate the health risks associated with the exposure of surgical implants to strong electromagnetic fields. The implant conductor assembly provided by the invention can minimise the induction of radio frequency currents within an implant conductor electrode lead.

The implant conductor assembly provided by the invention may be used with a wide variety of prior art implant conductor materials and may also provide safety advantages over a range of frequencies of alternating current. In particular the invention may safeguard surgical implant users from tissue heating and induced current effects in various situations ranging from exposure to MRI machines through to, for example, proximity to electrical welding machines or strong electromagnetic signal transmitters.

BRIEF DESCRIPTION OF THE DRAWINGS

Additional and further aspects of the present invention will be apparent to the reader from the following description of embodiments, given by way of example only, with reference to the accompanying drawings in which:

FIGS. 3a, b and c show midpoint cross-section views of the simulated magnitude of the magnetic field surrounding an insulated conductor in FIG. 3a, an electrode wire lead with single field target conductor in FIG. 3b, and an electrode wire lead flanked by two opposed field target conductors in FIG. 3c.

FIGS. 5a, 5b show heat generated plotted against various lengths of the lead when a single field target conductor is provided.

FIGS. 6a, 6b show heat generated plotted against various lengths of the lead when the electrode lead is adjacent to two opposed field target conductors.

FIGS. 7a, 7b show the temperature change of the distal electrode plotted against length of the electrode lead in the case of the single field target conductor arrangement of FIG. 5a.

FIGS. 8a, 8b show the temperature change of the distal electrode plotted against length of the electrode lead in the case of the dual field target conductor arrangement of FIG. 6a.

Further aspects of the invention will become apparent from the following description of the invention which is given by way of example only of particular embodiments.

BEST MODES FOR CARRYING OUT THE INVENTION

Figure 1:
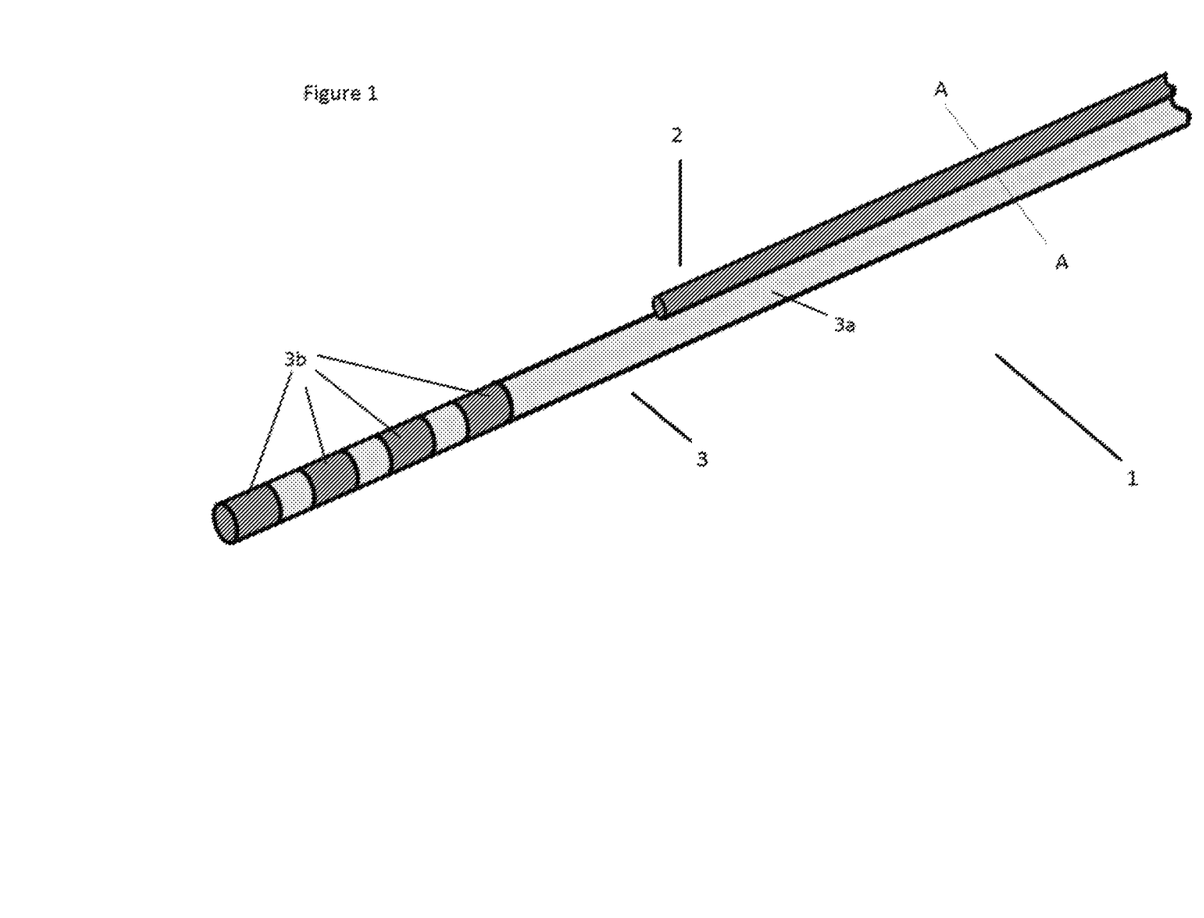
FIG. 1 provides a perspective view of one end of an implant lead assembly with a single field target conductor as provided in accordance with one embodiment of the invention.
Figure 2:
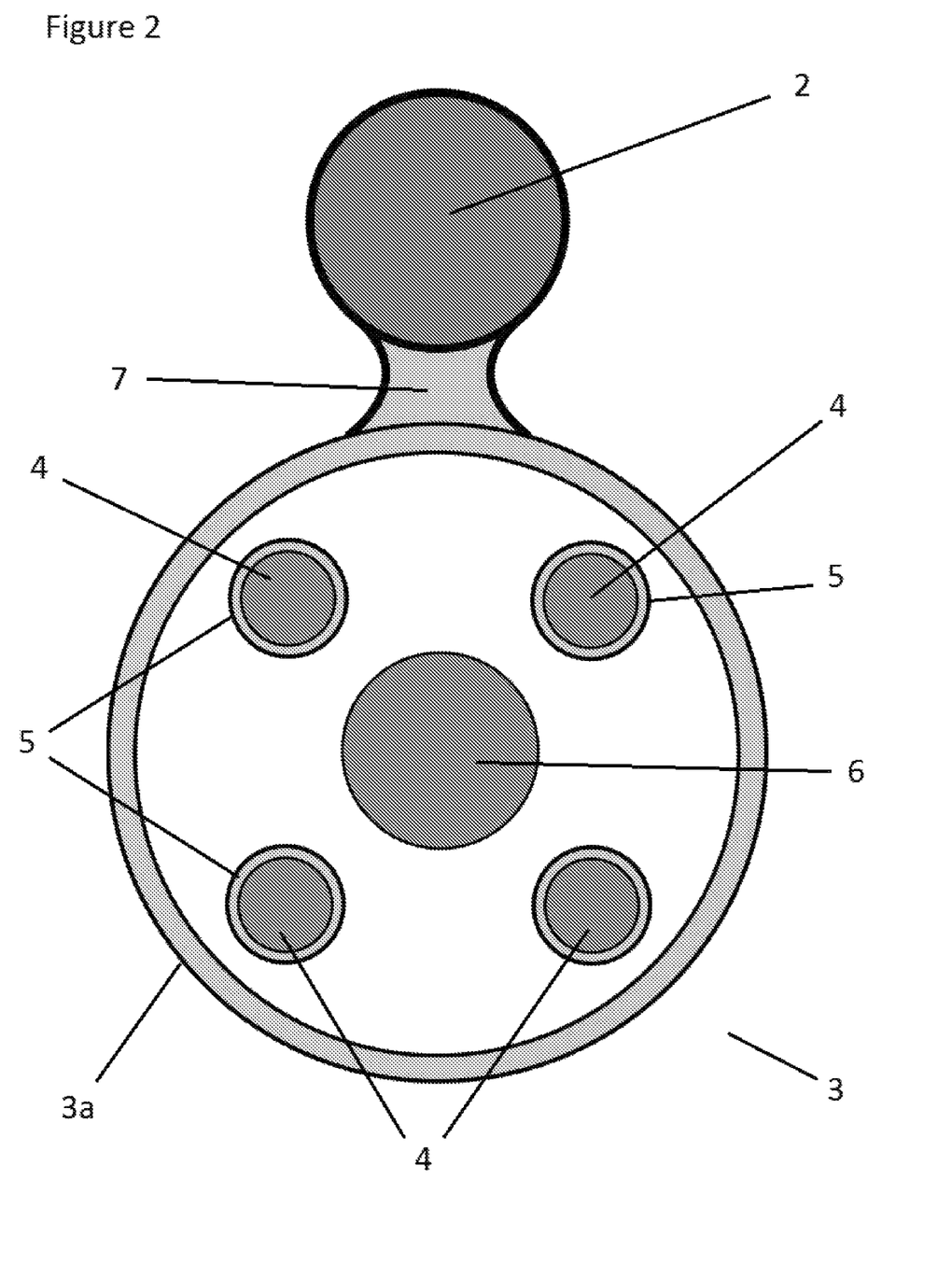
FIG. 2 provides a side cross section view through the assembly of FIG. 1 where marked at line A-A.

FIG. 1 provides a perspective view of one end of an implant lead assembly 1 which incorporates a single field target conductor 2 in accordance with one embodiment of the invention. FIG. 2 provides a side cross section view through the assembly 1 where marked at line A-A.

The implant conductor assembly 1 includes an electrode lead 3, and the single field target conductor 2 shown. The field target conductor 2 is located adjacent to the electrode lead 3 to mutually couple the field target conductor to the electrode lead. Surface portions 3a of the exterior of the electrode lead are coated in an electrical insulation jacket material, while exposed surface portions 3b form contact electrodes.

As can be seen from FIG. 2 the field target conductor 2 is formed from a solid length of conductive metal wire. The electrode lead shown incorporates four electrode conductors 4 surrounded by the jacket of electrical insulator material 3a which retains each electrode conductor in place within the electrode lead structure. These conductors 4 are able to move to a limited degree inside the insulator jacket 3a. Each of the four electrode conductors are also coated with a layer of insulation 5. A stylet 6 is provided to guide the entire assembly into the body of a recipient. Once the assembly is installed within a user the stylet is removed leaving a void in the interior of the electrode lead 3.

The field target conductor 2 is located to one side of the electrode conductor, thereby providing a parallel offset orientation to the longitudinal axes of each of the field target conductor 2 and electrode lead 3. A layer of adhesive 7 is used to locate the field target conductor 2 with its longitudinal axis parallel to the longitudinal axis of the electrode lead 3, where the longitudinal axis of each of the field target conductor and electrode lead are offset from each other.

This positioning of the electrode lead 3 and the relative lengths of each conductor act to concentrate electromagnetic fields in the vicinity of the assembly 1 towards the field target conductor 2. This interaction between the field target conductor and electrode lead is shown in more detail with respect to FIGS. 3a and 3b.

Figure 3:
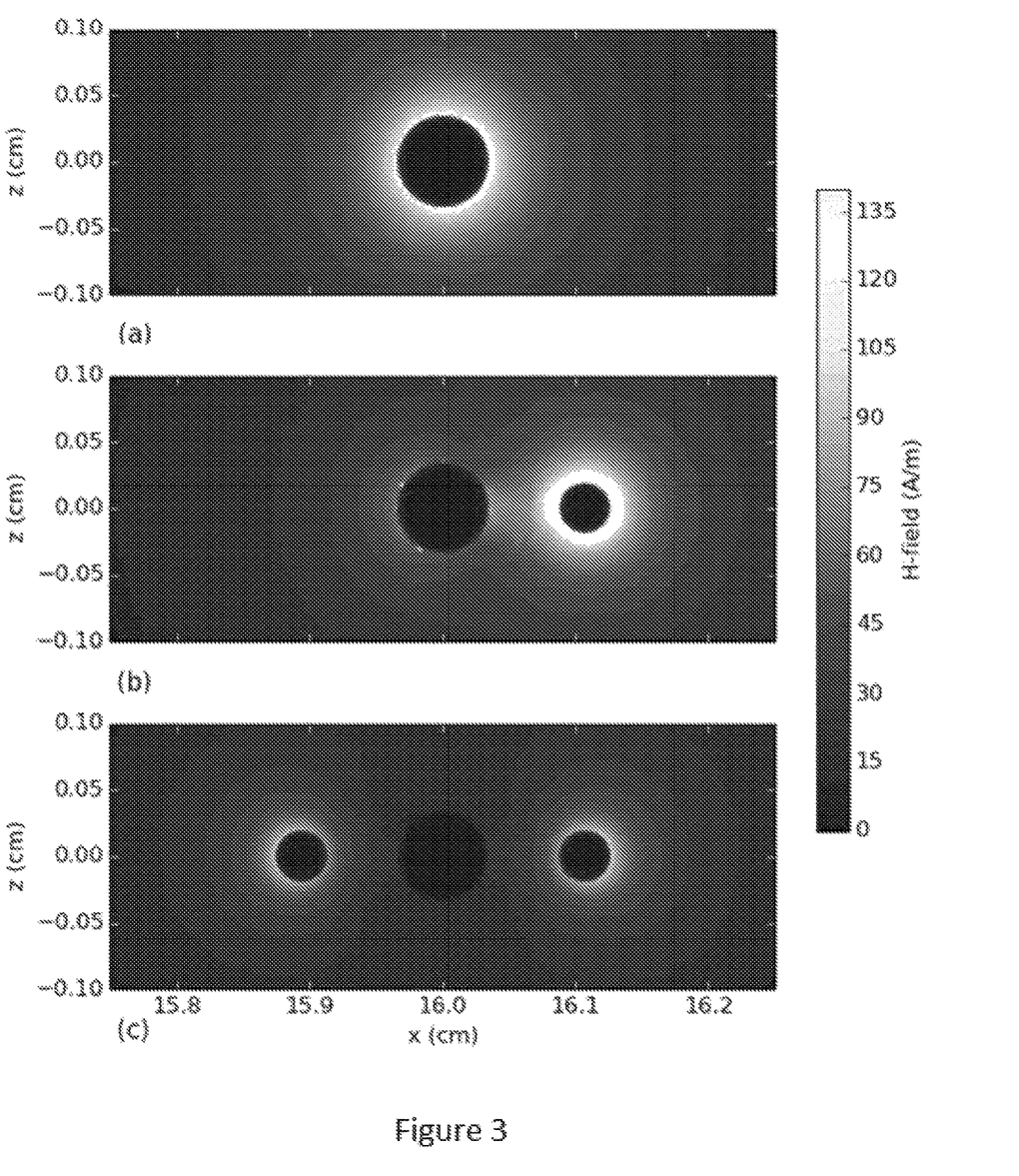

FIGS. 3a, b and c show midpoint cross-section views of the simulated magnitude of the magnetic field surrounding an insulated electrode lead in FIG. 3a, an insulated electrode lead with single field target conductor in FIG. 3b and an insulated electrode lead flanked by two opposed field target conductors in FIG. 3c. In each of these plots the total length, l, of the insulated electrode lead is 25 cm. FIG. 3b shows an insulated electrode lead with a single bare conductor 60% the length of the lead, while FIG. 3c shows two target field conductors which are 90% the length of the insulated electrode lead depicted.

FIG. 3a shows the magnetic field distribution for the electrode lead 3 in the absence of a field target conductor. As can be seen by this image the lead 3 acts as an antenna to concentrate the field intensity about the longitudinal axis of the lead.

FIG. 3b shows the distribution of the same magnetic field when the field target conductor is located adjacent to the electrode lead. As can be seen from FIG. 3b the field has been shaped by the combination with the adjacent conductor, with the field target conductor experiencing the areas of highest intensity when compared to that experienced by the electrode lead.

FIG. 3c shows the distribution of the same magnetic field when a pair of opposed field target conductors are located on opposite sides of the electrode lead. As can again be seen from FIG. 3c the field has been shaped by the combination of adjacent conductors, with the field target conductors experiencing the areas of highest intensity when compared to that experienced by the electrode lead.

Figure 4:
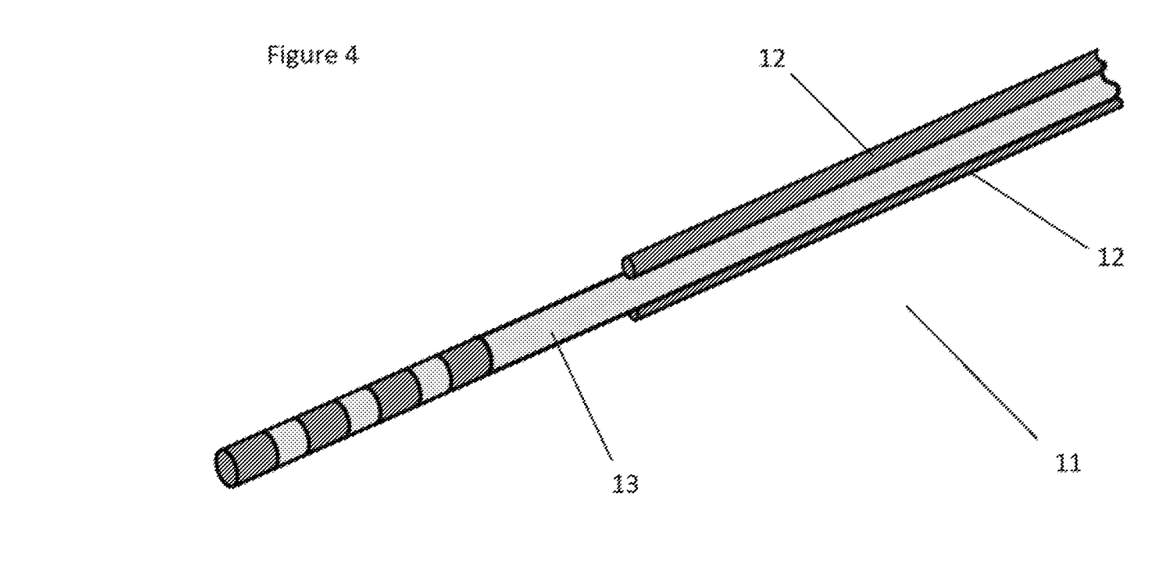
FIG. 4 provides a perspective view of one end of an implant lead assembly with multiple field target conductors as provided in accordance with an alternative embodiment to that shown with respect to FIGS. 1 and 2.

FIG. 4 provides a perspective view of one end of an implant lead assembly 11 with multiple field target conductors 12 provided in an alternative embodiment to that shown with respect to FIGS. 1 and 2. The magnetic fields experienced by this form of assembly are discussed with respect to FIG. 3c.

This alternative arrangement positions a pair of opposed field target conductors on either side of an electrode lead 13. The ends of each field target conductor are encapsulated by a plastic insulator material while the middle section of each conductor (not shown) is exposed to the body tissue of the recipient of the assembly.

In this embodiment each field target conductor has a length approximately 90% that of the electrode lead, allowing the electrode lead to shape and reflect electromagnetic fields towards each field target conductor.

Figure 5A:
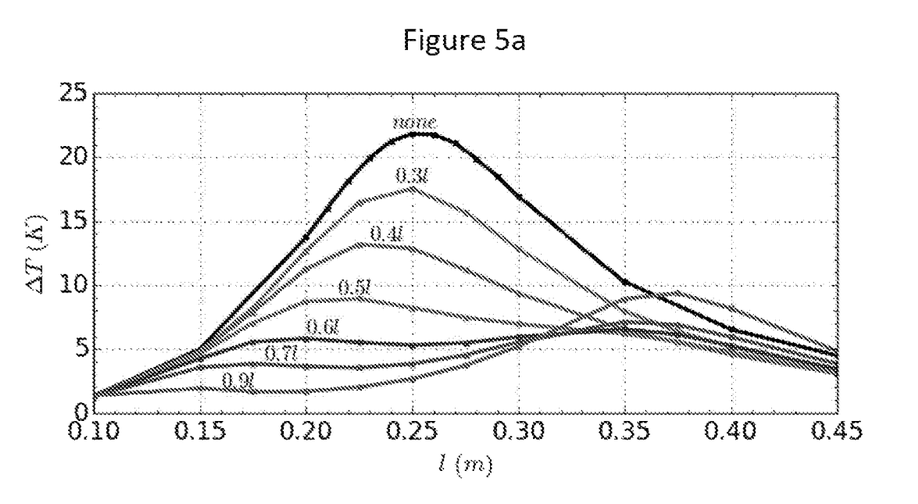
FIG. 5a shows temperature changes experienced at the distal electrode of the electrode lead when the electrode lead is adjacent to this single field target conductor.
Figure 5B:
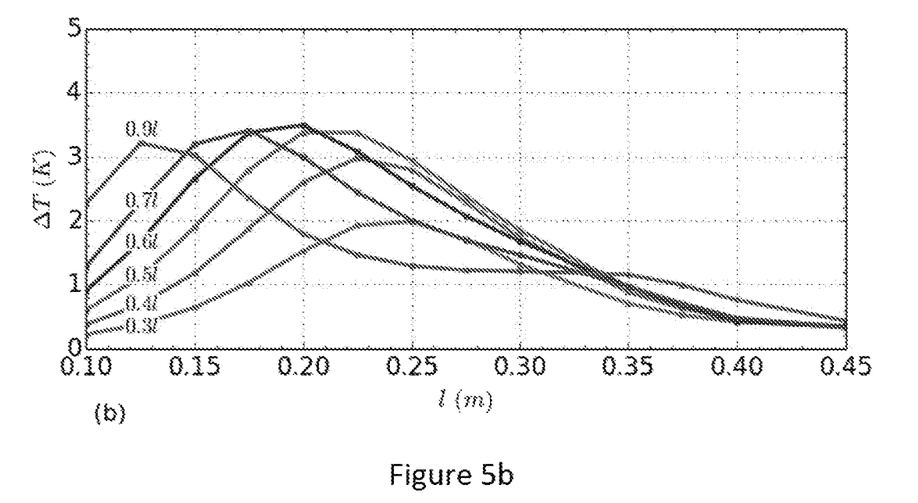
FIG. 5b shows temperature changes experienced in the single field target conductor located adjacent to an electrode lead.

FIGS. 5a, 5b show heat generated at the distal electrode plotted against various lengths of the lead when a single field target conductor is provided. FIG. 5a shows temperature changes experienced at the distal electrode of the electrode lead when the electrode lead is adjacent to this single field target conductor. FIG. 5b shows temperature changes experienced in the single field target conductor located adjacent to the electrode lead.

Field target conductor lengths are varied from 0.3-0.9 l to produce the data plotted, where a standard lead without a field target conductor has the profile denoted by "none".

FIG. 5(a) shows simulated predictions of the distal heating for an assortment of electrode leads with length l, each having a single field target conductor of specified fraction of this length. It is apparent a field target conductor of length 0.6l-0.7l produces the least amount of heating over the range.

The field target conductor itself experiences some heating along its length as is shown in FIG. 5(b).

Figure 6A:
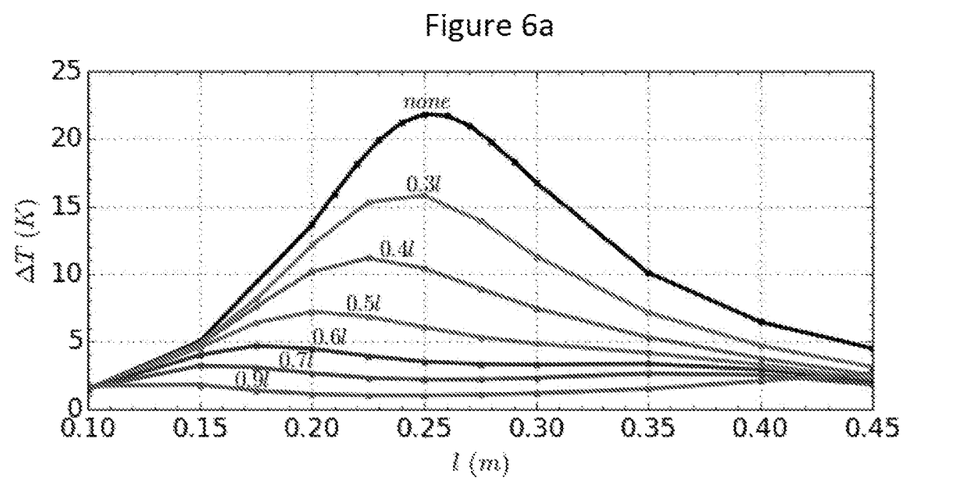
FIG. 6a shows temperature changes experienced at the distal electrode of the electrode lead when the electrode lead is adjacent to these two opposed field target conductors.
Figure 6B:
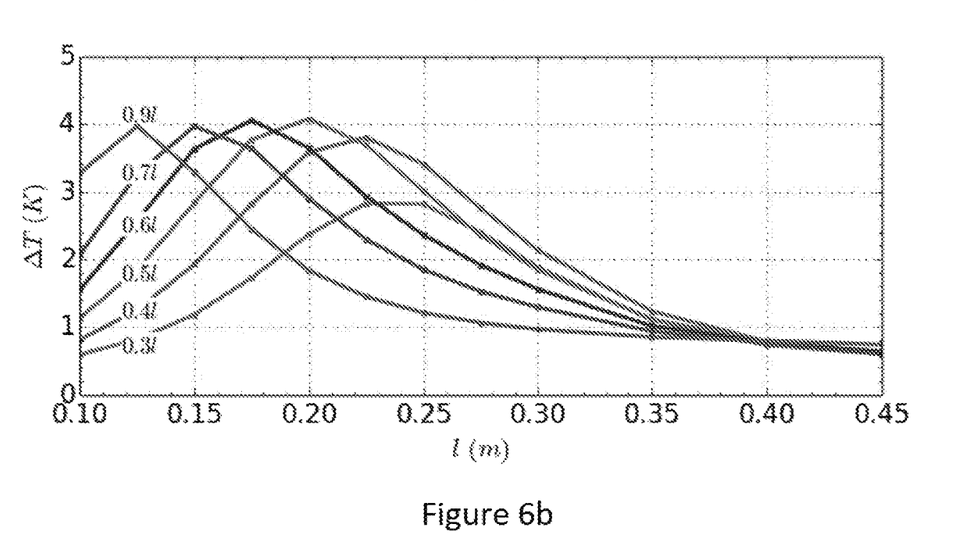
FIG. 6b shows heat generated by one of the two field target conductors when the electrode lead is adjacent to these two opposed field target conductors.

FIGS. 6a, 6b show heat generated plotted against various lengths of the lead when the electrode lead is adjacent to two opposed field target conductors. FIG. 6a shows temperature changes experienced at the distal electrode of the electrode lead when the electrode lead is adjacent to these two opposed field target conductors. FIG. 6b shows heat generated by one of the two field target conductors when the electrode lead is adjacent to these two opposed field target conductors.

Field target conductor lengths are varied from 0.3-0.9l to produce the data plotted, where a standard lead without a field target conductor has the profile denoted by "none". Distal heating is virtually eliminated for leads with two field target conductors as is shown FIG. 6(a), when the length of each equivalent field target conductor is between 0.7l-0.9.

Figure 7A:
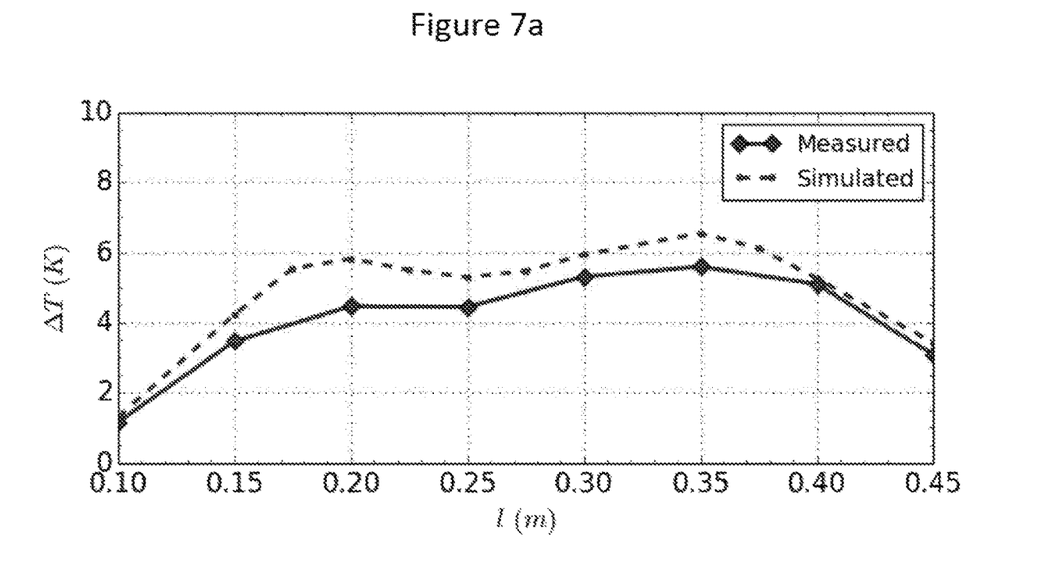
Figure 7B:
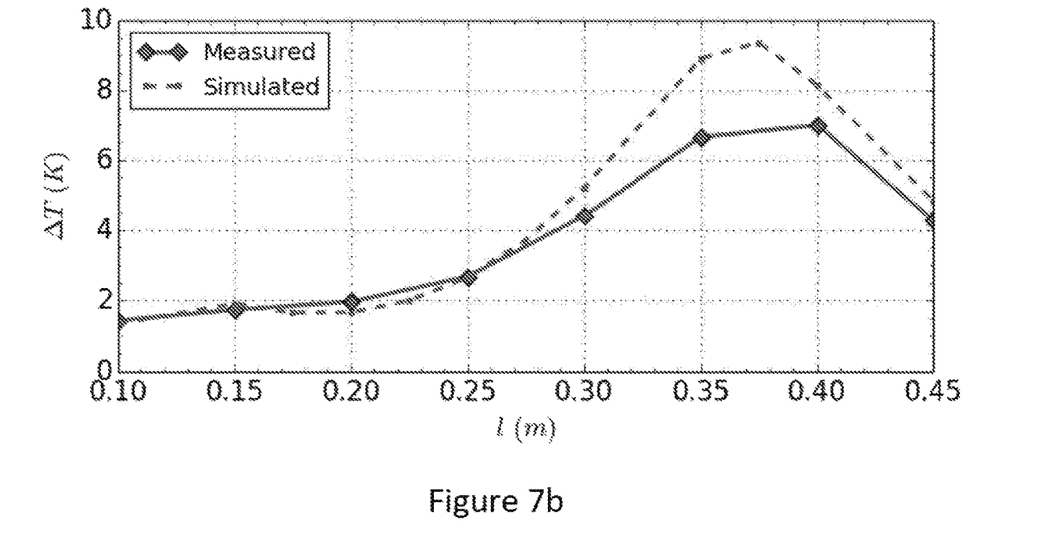

FIGS. 7a, 7b show the temperature change of the distal electrode plotted against length of the electrode lead in the case of the single field target conductor arrangement of FIG. 5a. The measured distal heating of electrode leads with a single 0.6l target conductor and a 0.9l target conductor are shown in FIGS. 7(a) and 7(b), respectively.

Figure 8A:
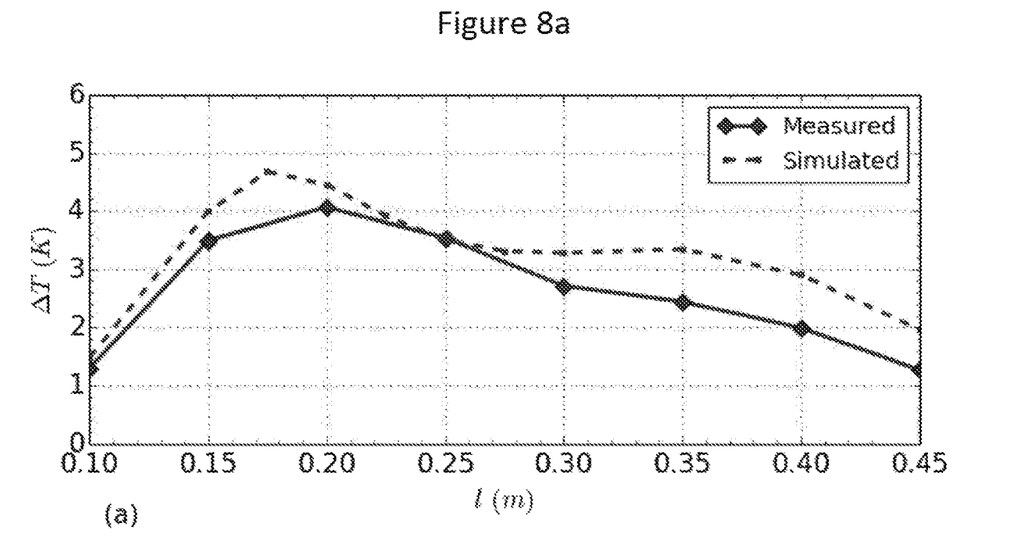
Figure 8B:
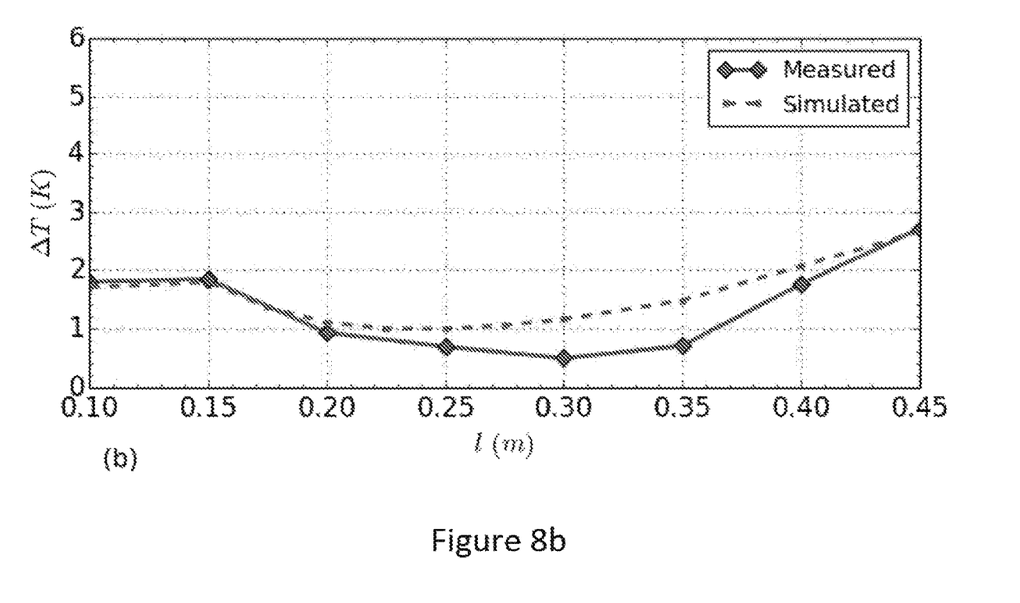

FIGS. 8a, 8b show the temperature change of the distal electrode plotted against length of the electrode lead in the case of the dual field target conductor arrangement of FIG. 6a. The measured distal heating of electrode leads with a 0.6l target conductor and a 0.9l target conductor are shown in FIGS. 8(a) and 8(b), respectively.

FIG. 8 shows an even greater reduction in distal heating when the same leads have a pair of opposed (and possibly identical) field target conductors.

Figure 9:
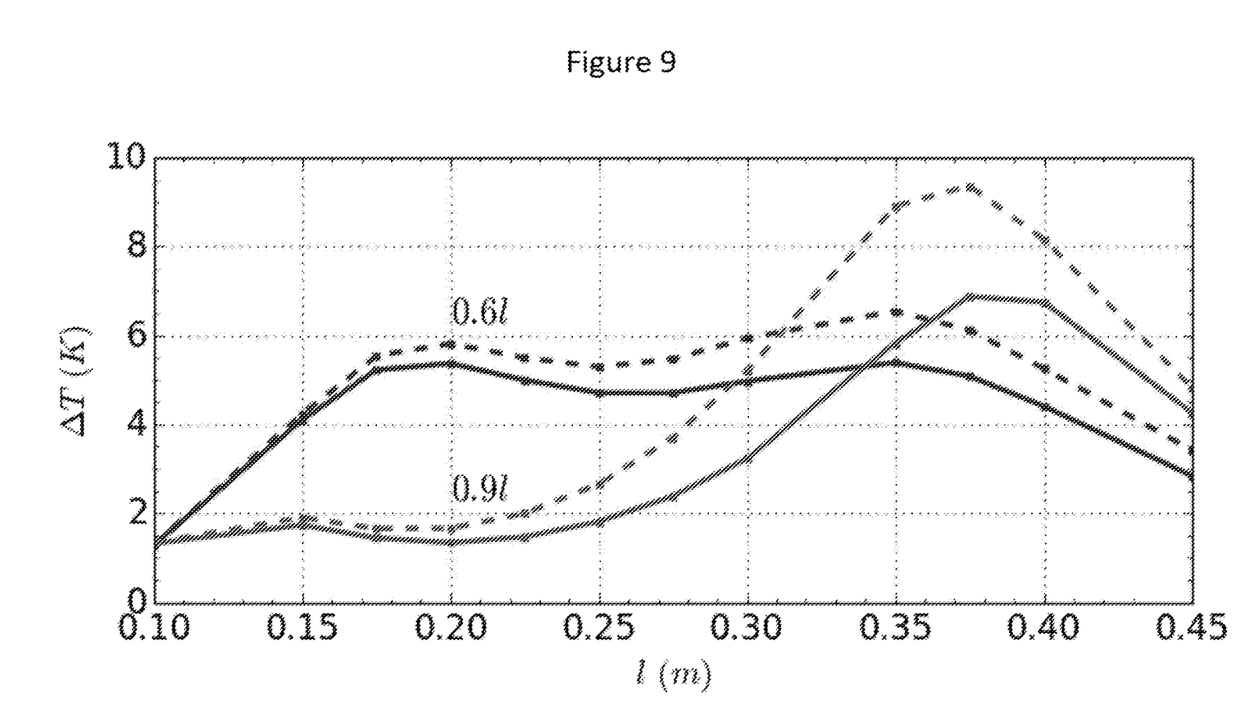
FIG. 9 shows a comparison of simulated predictions of heat generated at the distal electrode plotted against various lengths of the lead with differing diameter measurements.

FIG. 9 shows a comparison of simulated predictions of heat generated at the distal electrode plotted against various lengths of the lead with differing diameter measurements. This figure illustrates embodiments which include a single field target conductor with a length of either 0.6l or 0.9l. The dashed line traces illustrate the heat increase for target conductors with diameters of 0.4 mm, whereas the thicker variants have diameters of 0.8 mm. As shown, the field target conductors with the larger diameters result in less distal heating.

It is to be understood that the present invention is not limited to the embodiments described herein and further and additional embodiments within the spirit and scope of the invention will be apparent to the skilled reader from the examples illustrated with reference to the drawings. In particular, the invention may reside in any combination of features described herein, or may reside in alternative embodiments or combinations of these features with known equivalents to given features. Modifications and variations of the example embodiments of the invention discussed above will be apparent to those skilled in the art and may be made without departure of the scope of the invention as defined in the appended claims.

What we claim is:

1. An implant conductor lead assembly comprising:
   an electrode lead comprising at least one length of conductive material; and
   at least one field target conductor located adjacent to and spaced apart from the electrode lead such that a longitudinal axis of the at least one field target conductor is offset from a longitudinal axis of the electrode lead, the at least one field target conductor being located to mutually couple the at least one field target conductor to the electrode lead,
   wherein the electrode lead acts to concentrate electromagnetic fields in a vicinity of the implant conductor lead assembly towards said at least one field target conductor.

2. The implant conductor lead assembly as claimed in claim 1 wherein at least one field target conductor is positioned with its longitudinal axis parallel to the longitudinal axis of the electrode lead.

3. The implant conductor lead assembly as claimed in claim 1 wherein the field target conductor is formed from multi-stranded wire.

4. The implant conductor lead assembly as claimed in claim 1 wherein the length of the field target conductor is less than the length of the electrode lead.

5. The implant conductor lead assembly as claimed in claim 4 wherein the length of the field target conductor is less than the length of the electrode lead by half the wavelength of an expected electromagnetic field of an MRI machine.

6. The implant conductor lead assembly as claimed in claim 4 wherein the field target conductor has a length in the range of 40% to 90% of the length of the electrode lead.

7. The implant conductor lead assembly as claimed in claim 6 wherein the field target conductor has a length in the range of 50% to 70% of the length of the electrode lead.

8. The implant conductor lead assembly as claimed in claim 7 wherein the field target conductor has a length approximately equal to 60% of the length of the electrode lead.

9. The implant conductor lead assembly as claimed in claim 8 which includes the single field target conductor located adjacent to one side of the electrode lead and extending approximately 60% of the length of the electrode lead.

10. The implant conductor lead assembly as claimed in claim 4 which includes a pair of field target conductors.

11. The implant conductor lead assembly as claimed in claim 10 wherein the field target conductors are located on opposite sides of the electrode lead.

12. The implant conductor lead assembly as claimed in claim 10 or claim 11, wherein the field target conductors each extend at least 40% of the length of the electrode lead.

13. The implant conductor lead assembly as claimed in claim 12 wherein the field target conductors each extend at least 60% of the length of the electrode lead.

14. The implant conductor lead assembly as claimed in claim 13 wherein the field target conductors each extend approximately 90% of the length of the electrode lead.

15. The implant conductor lead assembly as claimed in claim 1 wherein at least one field target conductor is formed of a material having increased electrical resistance such that the energy of an MRI field is dissipated substantially evenly throughout the at least one field target conductor.

16. The implant conductor lead assembly as claimed in claim 1 which exhibits an electrical resistance ranging from 10-100000 Ohms/meter.

17. The implant conductor lead assembly as claimed in claim 1 wherein the ends of a field target conductor are sealed inside an electrically insulating material.

18. The implant conductor lead assembly as claimed in claim 1 wherein at least a portion of the exterior surface of a field target conductor is exposed to the body tissue of the recipient of the assembly.

19. The implant conductor lead assembly as claimed in claim 18 wherein substantially all of the exterior surface of the field target conductor is exposed to the tissue of an implant recipient.

20. The implant conductor lead assembly as claimed in claim 18 wherein at least the mid-point of the length of the conductor is exposed to the body tissue of the implant recipient.

21. A method of concentrating electromagnetic fields in a vicinity of an implant conductor lead assembly, the implant conductor lead assembly including an electrode lead comprising at least one length of conductive material and at least one field target conductor located adjacent to the electrode lead, the method comprising:
   mutually coupling the field target conductor to the electrode lead by offsetting a longitudinal axis of the at least one field target conductor from a longitudinal axis of the electrode lead such that the field target conductor is spaced apart from the electrode lead, wherein the electrode lead acts to concentrate electromagnetic fields in the vicinity of the implant conductor lead assembly towards said at least one field target conductor.

* * * * *